United States Patent [19]

D'Hinterland et al.

[11] Patent Number: 5,362,474
[45] Date of Patent: Nov. 8, 1994

[54] METHOD FOR DETECTING AND LOCATING INFLAMMATORY OR TUMOR FOCI IN A PATIENT AND DIAGNOSTIC KIT THEREFOR

[75] Inventors: Lucien D. D'Hinterland, Castres; Alain Le Pape, Langeais; Gérard Normier, Castres; Anne-Marie Pinel, Castres; Jacques Durand, Castres, all of France

[73] Assignee: Pierre Fabre Medicament, Paris, France

[21] Appl. No.: 910,677

[22] Filed: Jul. 8, 1992

Related U.S. Application Data

[62] Division of Ser. No. 491,184, Mar. 8, 1990, abandoned.

[30] Foreign Application Priority Data

Mar. 8, 1989 [FR] France ............................. 89 03034

[51] Int. Cl.$^5$ ..................... A61K 49/00; A61K 49/02
[52] U.S. Cl. .................................. 424/1.13; 424/7.1; 424/9; 424/1.73
[58] Field of Search ..................... 424/1.1, 9, 7.1, 1.73, 424/1.13; 514/23, 54, 8; 530/395; 536/53

[56] References Cited

U.S. PATENT DOCUMENTS

| | | | |
|---|---|---|---|
| 3,885,197 | 12/1974 | Hirsch et al. | 530/395 |
| 3,929,994 | 12/1975 | Hirsch et al. | 514/8 |
| 4,734,403 | 3/1988 | D'Hinterland et al. | 514/54 |
| 4,801,578 | 1/1989 | Monsigny et al. | 530/395 |
| 4,933,440 | 6/1990 | D'Hinterland et al. | 536/53 |
| 4,937,327 | 6/1990 | D'Hinterland et al. | 536/53 |
| 5,021,234 | 4/1991 | Ehrenfeld | 424/1.1 |

Primary Examiner—Robert L. Stoll
Assistant Examiner—Lara E. Chapman
Attorney, Agent, or Firm—Dressler, Goldsmith, Shore & Milnamow, Ltd.

[57] ABSTRACT

The present invention relates to an aerosol composition containing a carrier agent capable of recognizing and binding to inflammatory and tumor foci mobilizing macrophages in their immediate environment, and an aerosol substrate, characterized in that the said carrier agent consists of a polysaccharide compound selected from the compound D 25, extracted from the membrane proteoglycans of the bacterium *Klebsiella pneumoniae* and having a molecular weight of 30±0.10 Kd, and the compound oxidized D 25 in which the galactofuranoser residue (Gal$f$) of the linear polysaccharide chain of D 25 has been converted to arabinose, and their amide, ester or ether type derivatives, as well as their quaternary ammonium derivatives and salts, and also the derivatives obtained by grafting of phosphatides.

8 Claims, 6 Drawing Sheets

METHOD FOR DETECTING AND LOCATING INFLAMMATORY OR TUMOR FOCI IN A PATIENT AND DIAGNOSTIC KIT THEREFOR

This application is a division of application Ser. No. 07/491,184, filed Mar. 8, 1990, now abandoned.

The present invention relates to aerosol compositions containing a carrier agent capable agent capable of recognizing and binding to inflammatory and tumor foci mobilizing macrophages in their immediate environment, and an aerosol substrate.

More especially, the present invention relates to aerosol compositions for in vivo or ex vivo medical imaging or diagnosis, kits comprising such compositions and compositions for the targeted therapy of inflammatory and tumor foci mobilizing macrophages in their immediate environment.

According to their essential feature, the compositions according to the present invention contain a carrier agent consisting of a polysaccharide compound selected from the compound D 25, the compound oxidized D 25 which the galactofuranose residue (Gal$f$) of the linear polysaccharide chain D 25 has been converted to arabinose, and their amide, ester or ether type derivatives, as well as their as their quaternary ammonium derivatives and salts, and also their derivatives obtained by grafting of phosphatides.

The product designated D 25 is a polysaccharide compound extracted from bacterial membrane proteoglycans, composed essentially of galactose units and having a molecular weight of 30±10 kD. This polysaccharide has been described in French Patent No. 86/06,765.

It was presented as possessing immunostimulatory properties, in particular with respect to the induction of endogenous interferon and the activation of NK (Natural Killer) cells. This polysaccharide compound is preferably isolated from a non-encapsulated and nonpathogenic mutant strain of *Klebsiella pneumoniae* biotype a, deposited at the Collection Nationale de l'Institut Pasteur (Nationale Collection of the Pasteur Institute) under No. 145-I-IP.

The structure of D 25 contains, on the one hand a linear polysaccharide chain consisting of an approximately 5-fold repetition of a monomeric unit of 10 sugars, and on the other hand a single, more complex linking sequence to which short peptide chains are linked.

The monomeric repeating unit of the linear polysaccharide chain contains only galactose in the pyran and furan form in the following proportions: 3 β Gal p, 3 α Gal p, 2 β Gal f, 2 α Gal f.

The sequence of this monomeric unit is as follows:

linking structure.

The single linking structure is bound to the end of the linear polysaccharide chain. It contains glucose, galactose, glucosamine, heptose and mannodeoxyoctulosonic acid residues. Short peptide chains are linked to this structure.

The probable sequence is as follows:

The following amino acids making up the two associated peptide chains are present in the following numbers:

Aspartic acid: 3
Glutamic acid: 2
Serine: 1
Proline: 1
Glycine: 1.5
Alanine: 2
Valine: 1
Leucine: 1
Lysine: 1

Abbreviations

β Gal p = β-Galactopyranose
α Gal p = α-Galactopyranose
β Gal f = β-Galactofuranose
α Gal f = α-Glactofuranose
α Glc p = α-Glucopyranose
α Glc p NH$_2$ = α-Glucosamine
α Hep p = α-Heptose (D. manno-Heptose)
Man Oc. A = 3-Deoxy-D-manno-octulosonic acid

STRUCTURE OF D 25

The D 25 derivatives of the D 25 amide, ester or ether type, as well as the quanternary ammonium derivatives and salts according to the present invention, are semisynthetic derivatives of this compound, described in French Patent Application No. 86/06,765, now French Patent No. 2,598,434, as wellas in French Patent Application No. 87/05,690, now French Patent No. 2,614,306.

Among these components, there may be mentioned the derivatives of D 25 with acids, amines or alcohols having a fatty chain, that is to say possessing at least 4 alicyclic carbon atoms.

The derivatives of oxidized D 25 according to the present invention are also those in which at least a part of the galactofuranose (Galƒ) residues of the linear polysaccharide chain of D 25 have been converted to arabinose, without any other modification of the initial product.

Among these compounds, one is especially important, namely the compound in which all the galactofuranose residues of the linear polysaccharide chain have been converted to arabinose, and which is defined by the following monomer:

in which Gal p denotes galactopyranose (a and B forms) and Ara denotes arabinose (α and β forms).

Special interest also attaches to derivatives selected from the amides, esters, ethers or quaternary ammonium derivatives with an amide, acid or an alcohol of these oxidized D 25 compounds.

The D 25 derivatives are also obtained by grafting of phosphatides onto D 25 or its amide, ester and ether derivatives, as well as the quaternary ammonium derivative salts and the oxidized derivatives. They may be obtained from phosphatides such as egg or soya lecithins, hydrogenated lecithins, azolectins, cephalins, sphingosine and sphingomyelin, this list not being exhaustive and being capable of extension to other types of phospholipids bearing free amino or carboxy functions.

The compound D 25 and its derivatives have been shown to display an affinity for cells of the monocyte/macrophage type and, as a result, to make an ideal carrier agent for recognizing and binding to inflammatory and tumour foci mobilizing these cells. P As will be seen later, an essential feature of the compositions according to the present invention is that they are administered in the form of an aerosol. Trials carried out have, in effect, demonstrated that any administration route other than that employing an aerosol did not yield any satisfactory result.

It should, in addition, be noted that, most advantageously, the compound D 25 or its derivatives, administered by inhalation according to the present invention, does not require use to be made of a pharmaceutical dosage form and, in particular, does not need to be encapsulated in liposomes in order to be administered in the form of an aerosol.

The physiochemical properties of the product of the amphiphilic type permit direct pulmonary adsorption of the product.

In consequence, appropriately, the aerosol compositions according to the present invention will be intended more especially for in vivo or ex vivo imaging or diagnosis, for detecting inflammatory and tumour foci mobilizing macrophages in their immediate environment. Pathological foci of the order of millimeters in size may be detected.

The said polysaccharide compound of the composition selected from D 25 and its derivatives can then be labelled with a detectable component such as a radioactive, paramagnetic or fluorescent component.

The said polysaccharide compound of the composition can also be detectable indirectly, that is to say can be detected via a substance which is itself labelled with a detectable component as mentioned above, the said substance recognizing and binding specifically to the said polysaccharide compounds. By way of a substance recognizing and specifically binding to the said polysaccharide compounds, an antibody raised against the said compound may be mentioned.

The in vivo or ex vivo imaging or diagnostic kits according to the invention will hence contain either a composition in which the said polysaccharide compound is labelled, or a composition in which the said compound is not labelled and a second composition that may be injectable containing a substance recognizing the said polysaccharide compound, the said substance itself being labelled.

As a suitable radioactive component according to the invention, a radionuclide detectable by scintigraphy, such as technetium $^{99m}$Tc or alternatively, without implied limitation, $^{123}$iodine and $^{111}$indium, may be mentioned.

The aerosol compositions according to the present invention have proved most especially effective for in vivo imaging and diagnosis by scintigraphy.

The radionuclide may be detectable by visualization or by peroperative counting via a manually guided probe. The technique will then comprise a diagnosis by counting, not an imaging technique.

As a result of its sensitivity, scintigraphic imaging is, in many cases, the best technique permitting visualization of tumour or inflammatory foci smaller than one centimeter in size. It is generally based on the targeting of pathological cells, for example by means of drugs specifically recognized by a receptor or monoclonal antibodies specific for cell antigens, the tissue clearance of which must be rapid in order to permit good scintigraphic contrast from a minimal number of targeted cells, currently of the order of 5 to $7 \times 10^8$. To date, these constraints generally limited the possibilities of visualization for small tumours only detectable by the assay of their tumour markers, for example the Carcinoembryonic antigen (CAE) or Ca 15.3 and Ca 19.9.

According to the invention, another strategy for detecting small pathological foci is proposed, taking into account the very early existence, during tumour growth, of a recruitment, in the tumour itself and in its immediate environment, of immunocompetent cells, and mainly macrophages (EVANS R., Biochim. Biophys. Acta 1986, 865: 1–11; WEI W. Z. et al., Biochim. Biophys. Acta 1986, 865: 13–26; BUGESLKI P. J. et al., Am. J. Pathol. 1985, 118 419:424). The possibility of a scintigraphic visualization of tumours by the targeting of peritumoral macrophages via labelled antibodies directed towards differentiation antigens, for example the MAC 1 antigen corresponding to the C3bi receptor, has been attempted recently in the case of Lewis' tumour grafted in C57BL/6 mice (PELLEN P. et al., Immunobiol. 1986, 173: 197-198). This technique suffers, however, from the limitations of immunoscintigraphy, for which the high non-specific binding due to the poor tissue clearance of the antibody does not enable sufficient scintigraphic contrast to be obtained for the visualization of tumours of the order of millimeters in size (CHATAL J. F., Nucl. Med. Bio., 1986, 13: 203-205).

Improvement of the scintigraphic performance of a ligand capable of recognizing immunocompetent cells in vivo is hence highly dependent on its rate of tissue clearance.

In point of fact, specifically, the carrier agent according to the invention consisting of D 25 and its derivatives has not only been shown to be capable of combining mainly with cells of the mononuclear phagocyte system, such as blood monocytes, but also displays a high tissue clearance rate enabling sufficient scintigraphic contrast to be obtained for the visualization of tumours of the order of millimeters in size.

It will be noted that these results have led to an assessment of the efficacy of targeting of this cell type, in vivo, after intravenous injection in baboon apes of D 25 and its derivatives previously labelled with a gamma-emitting radioisotope such as $^{99m}$technetium, which is well suited to scintigraphic detection. In the 10 minutes following the injection, more than 80% of the injected product is trapped in the liver and spleen, very probably as a result of the sequestration of the polymeric forms of these compounds by cells of the reticular endothelial system. The intravenous route is hence unusable. However, as a result of the amphiphilic character of these molecules and the molecular mass of 30 KD of their monomeric units, an absorption takes place at the alveolar capillary barrier of the lung, thereby permitting a system administration of the active principle (ref.: ENNA S. J. and SCHANKER L. S., Am. J. Physiol., 1972, 223: 1227-31). For this reason, an essential feature of the compositions of the invention is their administration in the form of an aerosol.

Under optimized conditions of aerosol formation, passage of the labelled molecules into the blood stream is effective in 120±40 minutes with a blood half-life of the order of 140 minutes, elimination taking place via the urine. During the first 6 hours following the administration, the absence of a scintigraphic image of the thyroid permits the assertion that there is an absence of dissociation of the $^{99m}$Tc tracer which, in the free state, having the same ionic radius as the iodide ion, is rapidly accumulated in the thyroid cells. An experimental pathological model of a progressive ganglionic and pulmonary parenchymatous inflammatory reaction has been developed by inhalation of beryllium metal in the ape in order to assess the capacity of the compounds to target in vivo the immunocompetent cells in these lesions.

Under these experimental conditions, small peritracheal and mediastinal ganglia, most often smaller than 0.5 cm at autopsy, have been visualized in the 3 hours following the administration of a radioaerosol of D 25 or of oxidized D 25 derivative or of another derivative obtained by covalent coupling of phosphatide to D 25. At histological examination, the binding ganglia were characterized by an infiltration of macrophage cells laden with particles associated with a paracortical and follicular lymphoid depletion.

This binding is not linked to simple drainage via the tracheobronchial ganglia (ref.: HARMSEN A. G., Science, 1985, 230; 1277–80), since control scintigraphic experiments carried out under the same conditions with unilamellar liposomes radiolabelled with $^{99m}$technetium do not enable a ganglionic image to be obtained, this situation also applying to later stages of the examination.

In the case of animals having pulmonary granulomas confirmed at anatomopathological examination, a binding of D 25 and its derivatives is observed consistently in the pathological area, whereas conventional scintigraphic and radiological techniques (X-ray tomodensitometry, nuclear magnetic resonance imaging) have not been capable of revealing such lesions.

Assessment of the scintigraphic activity Of D 25 and its derivatives in human pathological conditions was undertaken after verification of the absence of a pyrogenic effect and a safety control in mice, rats and Papio papio apes. Scintigraphy was carried out in patients suffering from pulmonary tumours, metastasized or otherwise, and not previously treated, or from sarcoidosis with known mediastinal ganglionic involvement. These examinations were carried out in the Department of Nuclear Medicine of the Centre Hospitalier Universitaire de Tours (Tours University Hospital Centre) after obtaining the patients' informed consent. To avoid all risk of a hypersensitization complication, the examinations were performed only once on each patient, and no side effect, either clinical or biological, was observed. The results obtained, compared with those of other medical imaging examinations and, in operated subjects, with the histological data, show an intense binding of D 25 and its derivatives labelled with technetium, two to four hours after inhalation, in the mediastinal ganglia of the subjects suffering from sarcoidosis and the gangliotumoral complexes of various types of pulmonary tumours.

In a particular embodiment, the compositions or kits for imaging or diagnosis according to the invention are used for the detection of sarcoidosis, alveolitis granulomatosis, pneunocystosis, lung intersticial pathology, inflammatory and infectious lesions.

Due to its amphiphatic properties a rapid absorption by the lung alveolar barrier occurs when D 25 preparations are administered by aerosol. In a particular embodiment, the compositions or kit for imaging or diagnosis according to the invention are used for the isotopic exploration of lung functions such as ventilation and assessment of the integrity of the lung alveolar barrier by D 25 absorption. For these explorations the D 25 compositions are administered as an aerosol during a dynamic scintigraphy for example with an acquisition of 1 minute scintigraphic images during the inhalation (study of the ventilation) then for 30 minutes after the end of the administration (study of the D 25 lung clearance to assess the status of the alveolar barrier).

D 25 or its derivatives, labelled directly or detectable indirectly by a radionuclide and administered by inhalation, are also used according to the present invention for the detection and peroperative measurement of the activity of the binding foci in the context of the assessment of spread of the inflammatory or tumour conditions.

A use of D 25 or its derivatives administered by inhalation for studying by immunofluorescence, for example with an anti-D 25 antibody, the extent of the histiocytic reaction and the limits of the inflammatory and tumour foci in histopathology, may also be mentioned according to the present invention.

Finally, the subject of the present invention is also aerosol compositions for the therapy of inflammations and tumours mobilizing macrophages in their environment, characterized in that they contain the said polysaccharide compound, selected from D 25 and its derivatives, coupled, respectively, to an anti-inflammatory or antitumour active principle, administrable in the form of an aerosol.

Other advantages and features of the present invention will become apparent in the examples which follow.

EXAMPLE 1

Industrial Process for Obtaining D 25

D 25 is isolated from the membrane of a non-encapsuated and non-pathogenic strain of *Klebsiella pneumoniae*, biotype a, deposited under No. 145.I.IP at the collection of the Pasteur Institute in PARIS.

An industrial process especially developed for the large-scale production of D 25 is described below:

1.1 Production of clarified bacterial lysates

The biomass of *Klebsiella pneumoniae* is obtained by culturing in a fermenter in a liquid medium under conventional conditions; the only specific constraint being the abrupt arrest of growth by cooling to +4° C. at the end of the exponential growth phase in order to preserve the integrity of the biological structures.

The biomass is separated from the culture medium by continuous centrifugation in the cold state on a Sharples or Westfalia type industrial separator. After washing by resuspension in sterile physiological solution and centrifugation, the cell concentrate is stored frozen while awaiting treatment.

The bacterial concentrate is thawed in a reactor and suspended in Tris-HCl buffer (10 mM) pH 7.0 containing $MgCl_2$ (10 mM) and NaCl (0.15M) at 4° C. so as to have a final concentration equivalent to 50 g of dry cells per liter of suspension. 5 mg of DNase per liter of suspension are then added.

The microbial cells are then disintegrated continuous passage through APV Manton Gaulin type industrial grinders. The bacterial lysate thereby obtained is subjected to a first continuous clarification at $15,000 \times g$ on a Sharples separator at 4° C. in order to remove the grinding residues and the unground microorganisms. The centrifugation pellet is removed and the supernatant collected; it constitutes the clarified lysate.

1.2 Production of the membrane proteoglycan of *Klebsiella pneumoniae*

The clarified lysate obtained above is acidified with acetic acid to pH 4.2±0.2 and left standing for 30 minutes at +4° C. The precipitate of impurities formed is removed by continuous centrifugation on a Sharples at $15,000 \times g$. The clear supernatant containing the membrane proteoglycan is neutralized and then dialysed with distilled water by ultrafiltration across a membrane cutting off at 10,000 daltons, so as to have a resistivity of not less than 1,000 $\Omega$ cm$^{-1}$.

1.3 Production of D 25

The membrane proteoglycan is a high molecular weight polymer ($>1.5 \times 10^6$ daltons). It is depolymerized by controlled alkaline hydrolysis for 1 hour at 56° C. in 0.5M sodium hydroxide, then cooled and neutralized.

The contaminant wall fractions and proteins are then removed by an enzymatic digestion under the following conditions:

Tris q.s. 10 mM and EDTA q.s. 4 mM are added to the suspension and the pH is then adjusted to 7.0. 0.1 g/l of proteinase K and 0.1 g/l of lysozyme are then added and the mixture is incubated for 2 hours at 37° C. with stirring.

The D 25 is then purified by two consecutive precipitations with 2 volumes of ethyl alcohol at −20° C. in the presence of 0.5M sodium acetate, the precipitate obtained after standing for 30 minutes being collected by continuous centrifugation at $15,000 \times g$.

The final precipitate of D 25 is taken up in distilled water at 4° C. and the solution clarified by centrifugation at $30,000 \times g$ for 60 minutes. The supernatant is collected and then dialysed with distilled water to a resistivity of not less than 2,500 $\Omega$ cm$^{-1}$ by ultrafiltration across a membrane cutting off at 10,000 daltons.

The dialysate thereby obtained is sterilized by filtration through a 0.22 $\mu$m membrane and then lyophilized under sterile conditions. This lyophilisate constitutes the D 25.

Each industrial operation is carried out on samples of biomass corresponding to 2 to 4 kg of dry cells, and enables from 40 to 100 g of pure D 25 to be obtained.

EXAMPLE 2

Production of Semi-Synthetic Derivatives of D 25

2.1 Immunomodulators obtained by partial synthesis from D 25 have already been described in Patent No. 86/06,765 of May 2, 1986.

2.2 A derivative of oxidized D 25 in which the galactofuranoses of the polysaccharide chain have been converted to arabinoses has also been described in French Patent Application No. 87/05,690 of Apr. 22, 1987, now French Patent No.2,614,306.

A solution of purified D 25 is diluted in order to obtain 20 g of polysaccharide per liter of solution. 0.1M sodium acetate is then added and the pH is adjusted to 3.8.

15 g of sodium metaperiodate are then added per liter of solution, and the mixture is thereafter kept stirring for 48 hours in the dark and at a temperature of 15° C.

The excess metaperiodate is then removed by precipitation with barium hydroxide in the form of a concentrated solution added gradually with stirring until precipitation is complete. The precipitate thereby formed is removed by simple filtration.

21.6 g of $NaBH_4$ are then added to the above filtrate and the mixture is thereafter left to react for 18 hours at room temperature. The excess $NaBH_4$ is then destroyed by adding acetic acid to neutrality.

The solution obtained is dialysed, concentrated across a membrane cutting off at 10,000 daltons and then lyophilized. The lyophilisate thereby obtained constitutes the oxidized D 25 derivative.

2.3 New derivatives obtained by grafting of phosphatides onto D 25, possessing novel properties, in particular in respect of their pharmacokinetics and their intestinal absorption, were created.

They may be obtained from phosphatides such as egg or soya lecithins, hydrogenated lecithins, azolectin, cephalins, sphingosine and sphingomyelin, this list not being exhaustive and being capable of extension to other types of phospholipids bearing free amino or carboxy functions.

Coupling of a hydrogenated lecithin to D 25

2.3.1. Activation of D 25 with EDAC (1-ethyl-3-(3-dimethylaminopropyl)carbodiimide hydrochloride).

100 mg of D 25 are dissolved in 10 ml of distilled water, 25 mg of EDAC, dissolved beforehand in 2 ml of distilled water, are then added and the pH of the reaction is adjusted to 4.75.

2.3.2. After 30 minutes' stirring at pH 4.75, a solution of 100 mg of hydrogenated lecithin (lecinol S.10, Noorden) in 10 ml of THF is added, and the reaction mixture is kept stirring overnight.

2.3.3. The reaction mixture is then evaporated under vacuum and the residue obtained is extracted 3 times with chloroform to remove the excess unreacted lecithin.

2.3.4. After extraction with chloroform, the residue is taken up in distilled water, then dialysed and lyophilized.

The degree of coupling of lecithin to D 25 is then determined by spectrophotometric assay with the Boehringer diagnostic kit.

Under the experimental conditions described above, it is 5.8%.

By altering the excess of lecithin in the reaction medium, it is possible to adjust the hydrophobic character of the derivatives obtained.

EXAMPLE 3

Radiolabelling of D 25 and its Derivatives

In a penicillin type flask devoid of air, 1 mg of lyophilized product is dissolved in 1 ml of isotonic NaCl solution buffered to pH 7.2 with phosphates or with 0.01M Tris and outgassed beforehand under vacuum. The solution is then transferred, without introduction of air, into another flask of the same type containing 195 μg of stannous chloride freshly lyophilized (SIN, M. S. et al., J. Nucl. Med., 1971, 12: 204–208) from a stock solution prepared in 2N HCl, under vacuum.

After 10 minutes' reduction with intermittent stirring, labelling is carried out by the addition, without introduction of air, of 1110 to 1480 MBq of technetium-99 m in the form of sodium pertechnetate freshly eluted from a generator (CEA, ORIS). The final volume is adjusted to 4 ml by adding isotonic solution buffered to pH 7.2 and outgassed.

In 15 minutes at 18°–20° C. with intermittent stirring, labelling is complete with an efficiency, monitored by radio-HPLC on a TSK 2000 column, of more than 99.5%.

In the labelling flask, protected from air, the Tc-D 25 bond is stable for 1.5 hours, but the stability is reduced to approximately 30 minutes after distribution in a syringe.

Scintigraphic monitoring carried out after intravenous injection of the preparation into rats and rabbits does not detect significant thyroid binding of free $^{99m}$technetium in the 3 hours following injection. The labelled D 25 preparation is pyrogen-free according to the tests carried out in vivo in rabbits.

EXAMPLE 4

Administration of the Radiolabelled Product by Inhalation

D 25 or its radiolabelled derivatives are administered in the form of an aerosol under nebulization conditions which have to comply with the stability of the labelling and generate particles of a size compatible with a satisfactory transfer efficiency in the pulmonary alveoli. A TV 6000 ultrasonic inhaler (SIEMENS) operating at a frequency of 100 kHz or a FISONEB ultrasonic device (FISONS) operating at a frequency of 1,5 MHz can preferably be used. The solution is nebulized at a rate of 0.5 ml per minute. Inhalation is carried out for 15 minutes in a special hood surrounding the patient's head in order to prevent any contamination of the air by the aerosol fraction not inhaled or partially exhaled. Monitoring by dynamic scintigraphy carried out on the lungs during inhalation has enabled the effective transfer of the labelled product in the lung to be assessed at 5–7.5% of the initial dose.

EXAMPLE 5

Production of Scintigraphic Images

Scintigraphy is carried out in experimental pathology, as with patients, 2, 3 and 4 hours after inhalation. A gamma camera set to the photoelectric peak of 140 kev of $^{99m}$technetium is placed at the areas of interest, incidence being anterior and posterior. Image acquisition is preferably carried out with a matrix of 128×128 pixels. The images are then computer-processed to adjust the contrast and determine the scintigraphic ratio of the binding foci relative to the activity of reference areas, generally in the contralateral position.

EXAMPLE 6

Results Obtained in Experimental Pulmonary Berylliosis in Apes

Experimental berylliosis is a model of pulmonary granulomatosis, closely resembling human sarcoidosis in both its clinical and immunological features (KRIEBEL D. et al., Am. Rev. Respir. Dis. 1988, 137: 464–73) which has been especially well documented in animals by ANDRE S. (Doctoral Thesis in Biology, Univ. Paris Val de Marne 1984). We used adult Papio papio apes contaminated for 3 to 12 months by deposition of beryllium metal in the lower lobe of the right lung. The animals were explored regularly by scintigraphy of the pulmonary ventilation (DTPA-technetium) and pulmonary perfusion (albumin macroaggregates-technetium) functions, and by thoracic radiography, X-ray tomodensitometry and nuclear magnetic resonance imaging.

Scintigraphy with D 25 or its semi-synthetic derivatives was carried out after labelling 1 mg of product with 740 MBq of technetium-99 m.

Figure 1:
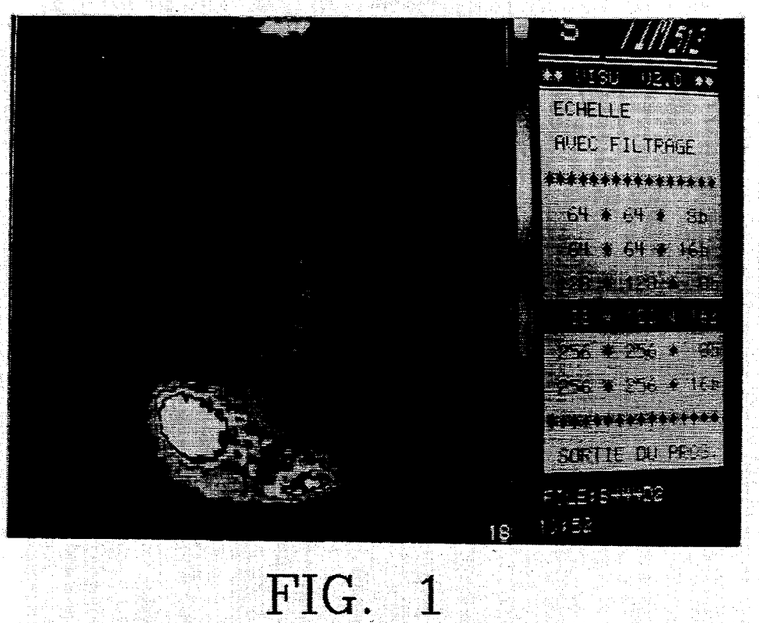
FIG. 1 shows scintigraphy with D 25, thorax dorsal surface, 3 h after inhalation, of baboon No. 444, 3 months after induction of a pulmonary berylliosis.
Figure 2A:
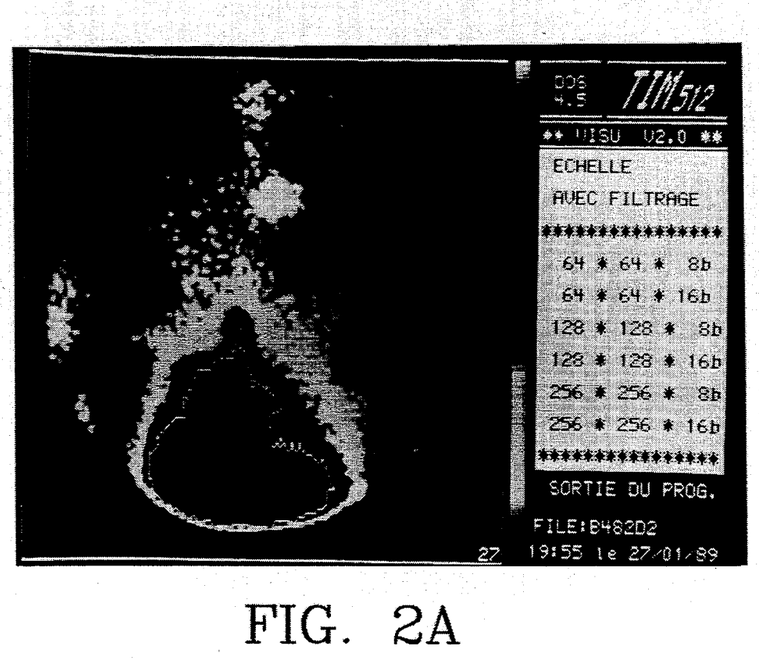
FIG. 2a shows scintigraphy with D 25 at the stage where the disease has progressed, the anatomical check being shown in FIG. 2b.
Figure 2B:
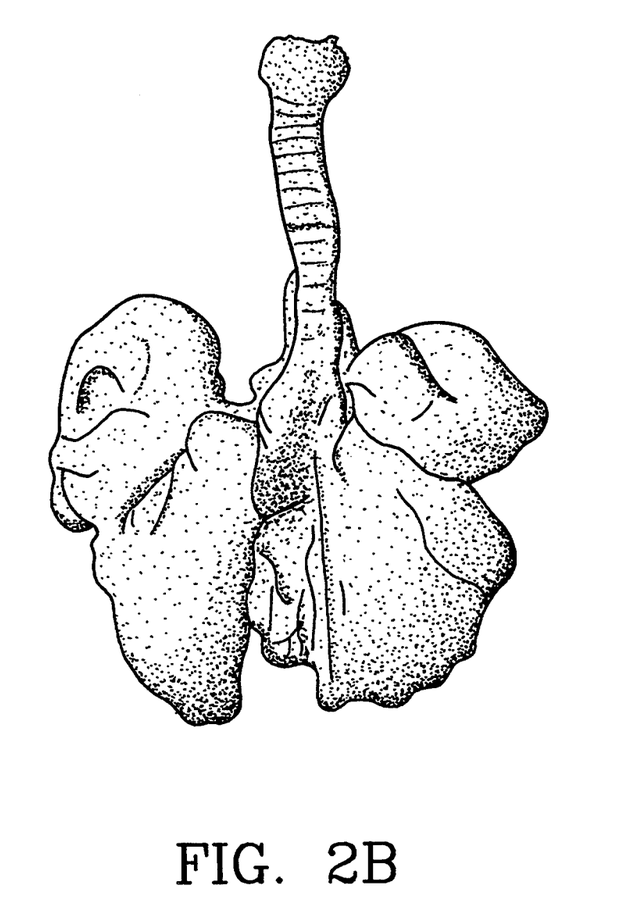

FIG.1:
  Baboon No. 444, 3 months after induction of a pulmonary berylliosis.
  Scintigraphy with D 25, thorax dorsal surface, 3 hours after inhalation.
  A hyper-binding in the lower lobe of the beryllium contaminated right lung exhibiting an alveo lytis (1st at stage of the disease) is observed FIG. 2:
  2a: Baboon No. 482, 1 year after induction of a pulmonary berylliosis.
  Scintigraphy with D 25, thorax dorsal surface, 2 hours after inhalation.
  A right paratracheal binding localized in the retrocarinary paratracheal ganglia (2nd stage of the disease) is observed.
  2b: Autopsy specimen showing the presence of inflammatory retrocarinaryganglia 8×3 mm in size induced by the berylliosis, in the area binding in scintigraphy with D 25.

EXAMPLE 7

Results Obtained in Human Pathology

Figure 6:
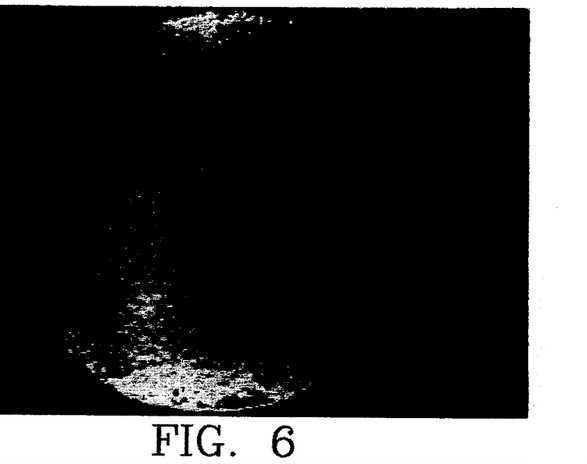
FIG. 6 shows scintigraphy with D 25, thorax dorsal surface, 4 h 30 min after inhalation, the patient suffering from bilateral pulmonary metastases.
Figure 7:
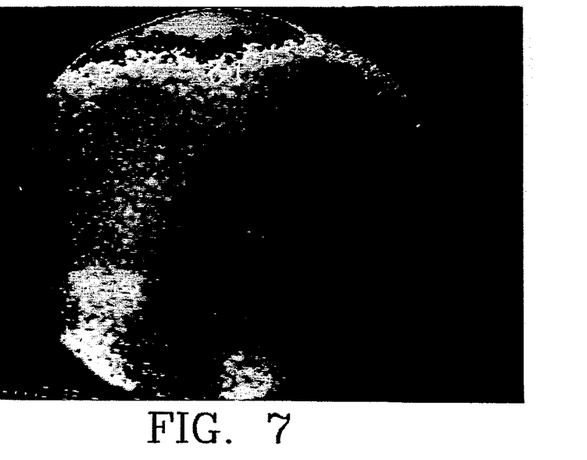
FIG. 7 shows scintigraphy with D 25, 4 hours after inhalation, of the thorax dorsal surface, the patient suffering from a carcinoma of the lower left lobe.

D 25 is used at a dose of 1 mg after labelling with 1110 MBq of technetium.

a) In sarcoidosis
  6 patients were explored by comparing scintigraphy with aerosol D 25 with that of gallium-67 citrate injected i.v.
  In 3 patients suffering from an increase in size of the thoracic ganglia and the reticulonodular foci, scintigraphic imaging of the hilar ganglia with D 25, 4 hours after inhalation (FIG. 3A), is identical to that of gallium, 48 hours after i.v. injection (FIG. 3B).
  In 3 other patients suffering from a diffuse pulmonary condition without ganglionic abnormalities visible in X-ray tomodensitometry, scintigraphy with D 25 shows a diffuse hyperactivity of the lungs (FIG. 4A) whereas scintigraphy with gallium displays a markedly lower scintigraphic contrast in the same areas of interest (FIG. 4B), whether the condition is observed at the intermediate stage II or in a phase of progressive fibrosis corresponding to stage III (FIG. 5).

b) In pulmonary tumours
  Scintigraphy with D 25 carried out on 15 patients detected in 8 of the latter significant binding in the pulmonary metastases (FIG. 6), the hilar tumours, the mediastinal ganglia and the gangliotumoral complexes (FIG. 7). Two peripheral metastatic localizations, one of them ganglionic (FIG. 8) and the other cutaneous (FIG. 9) were also detected. No binding of D 25 was observed in an undiseased area.

c) In pulmonary pneumocystosis
  4 patients contaminated with HIV virus and suffering from pulmonary pneumocystosis, confirmed by bronchoalveolar lavage and not yet treated, were explored by scintigraphy with aerosol D 25. In 3 of them, a pulmonary activity persisting beyond 4–5 hours after inhalation was observed, including in the pulmonary regions exhibiting defective ventilation shown objectively by pulmonary radiography or scintigraphy of the ventilation by inhalation of $^{99m}$technetium-labelled DTPA.

Figure 3A:
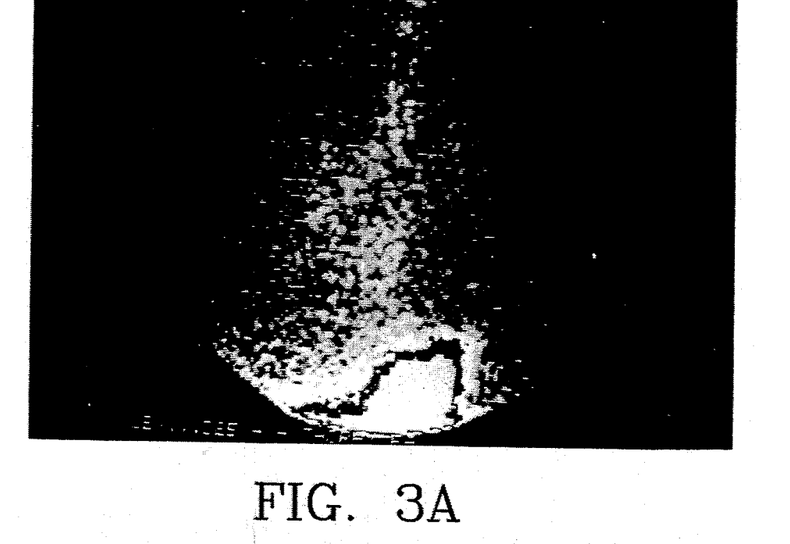
FIGS. 3a and 3b show, in a patient suffering from stage I sarcoidosis with an increase in the size of the thoracic ganglia and reticulonodular foci, the scintigraphic imaging of the hilar ganglia with D 25 4 hours after inhalation (FIG. 3a) and that with gallium performed 48 hours after i.v. injection (FIG. 3b).
Figure 3B:
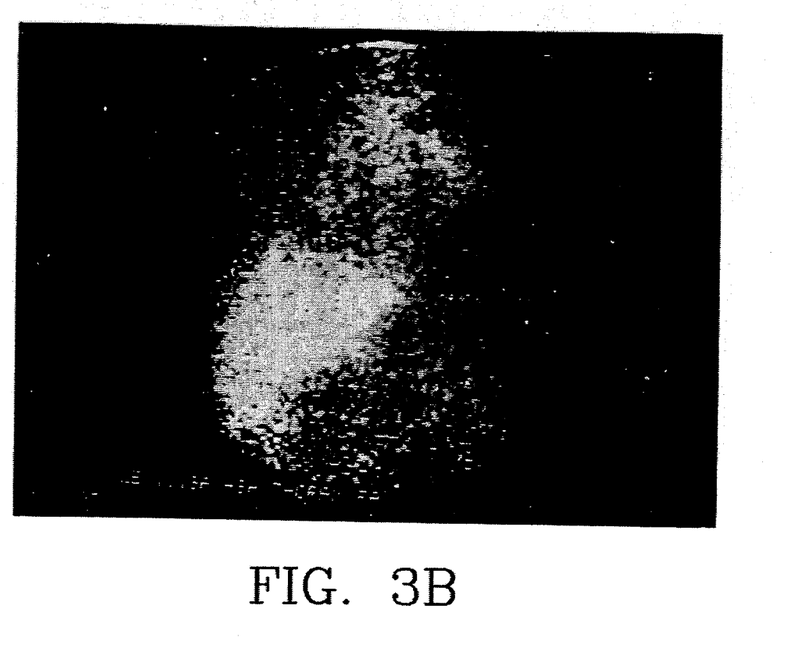

FIG. 3: Patient LEV . . . suffering from stage I sarcoidosis with mediastinal adenopathy.
  3a: Scintigraphy with aerosol D 25, 4 hours after inhalation, thorax ventral surface. Mediastinal binding associated with diffuse pulmonary activity.
  3b: Scintigraphy with gallium citrate, 48 hours after intravenous injection. Thorax ventral surface (mediastinal binding+pulmonary activity).

Figure 4A:
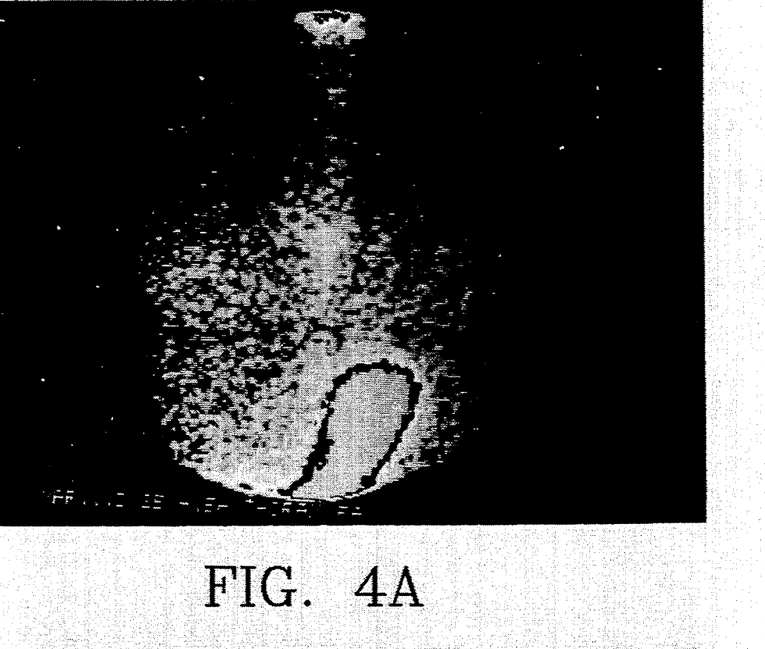
FIGS. 4a and 4b show a patient suffering from stage II sarcoidosis corresponding to a diffuse pulmonary pathological condition without ganglionic abnormality, scintigraphy of the lungs with D 25 (FIG. 4a) and scintigraphy with gallium (FIG. 4b).
Figure 4B:
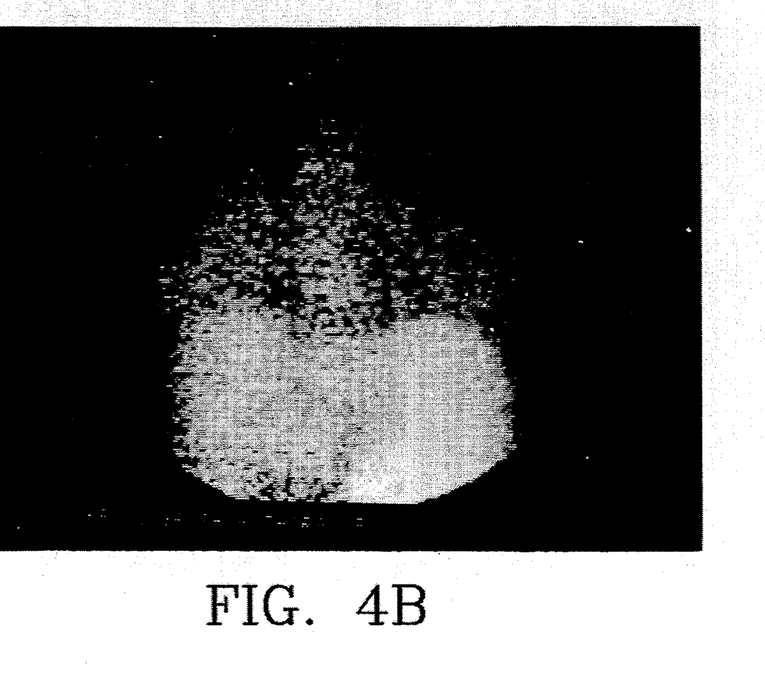
Figure 5:
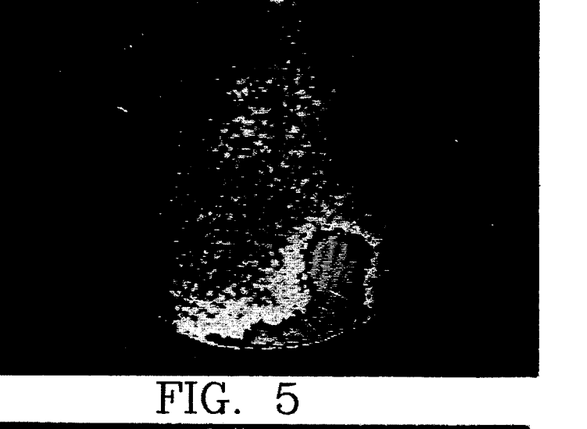
FIG. 5 shows scintigraphy with D 25, 4 hours after inhalation, of a stage III sarcoidosis which has progressed to the stage of fibrosis with inflammatory lesions but without a ganglion.

FIG. 4: Patient NAR . . . suffering from stage II sarcoidosis.
  4a: Scintigraphy with aerosol D 25, 4 h 30 min after inhalation, of the thorax ventral surface (binding by both lungs, more pronounced in the bases).
  4b: Scintigraphy with gallium citrate, thorax ventral surface, 24 hours after intravenous injection.

FIG. 5: Patient DJE . . . suffering from stage III sarcoidosis with progressive fibrosis and inflammatory lesions.
  Scintigraphy with aerosol D 25, 4 hours after inhalation, of the thorax ventral surface showing a very pronounced binding over the whole of the pulmonary area.

FIG.6: Patient TEL . . . : bilateral pulmonary metastases (release of balloons) of a cylindroma of the facial bones.
  Scintigraphy with aerosol D 25 (thorax dorsal surface) 4 h 30 min after inhalation reveals a hyperactivity of the tracer in both lungs.

FIG. 7: Patient NEU . . . epidermoid carcinoma of the lower left lobe. 4 hours after inhalation of D 25, scintigraphy of the thorax dorsal surface shows a focus of intense binding in the tumour area.

Figure 8:
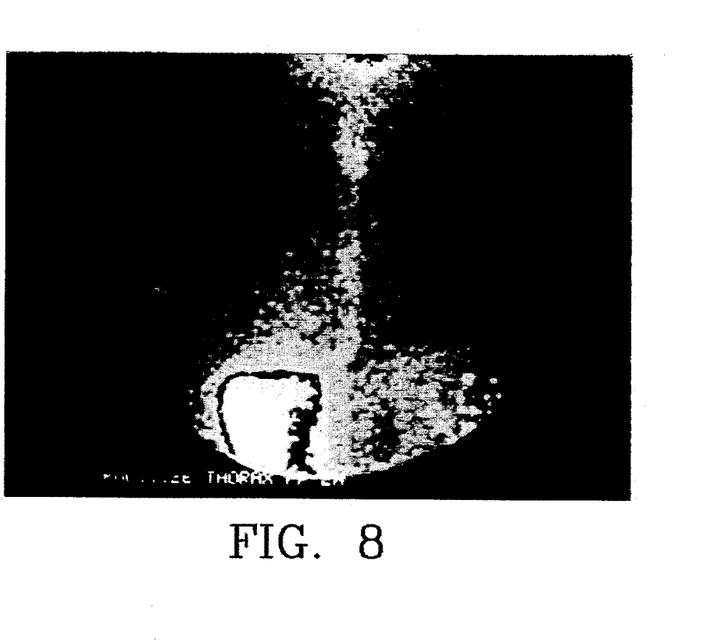
FIG. 8 shows the scintigraphy with D 25, 4 hours after inhalation, of a ganglionic localization of a patient suffering from a large-cell adenocarcinoma of the upper lobe of the right lung.

FIG. 8: Patient ROC . . . : metastasis of a large-cell adenocarcinoma of the upper lobe of the right lung. Detection by scintigraphy with D 25, 4 hours after inhalation, of an axillary ganglionic localization, confirmed histologically.

Figure 9:
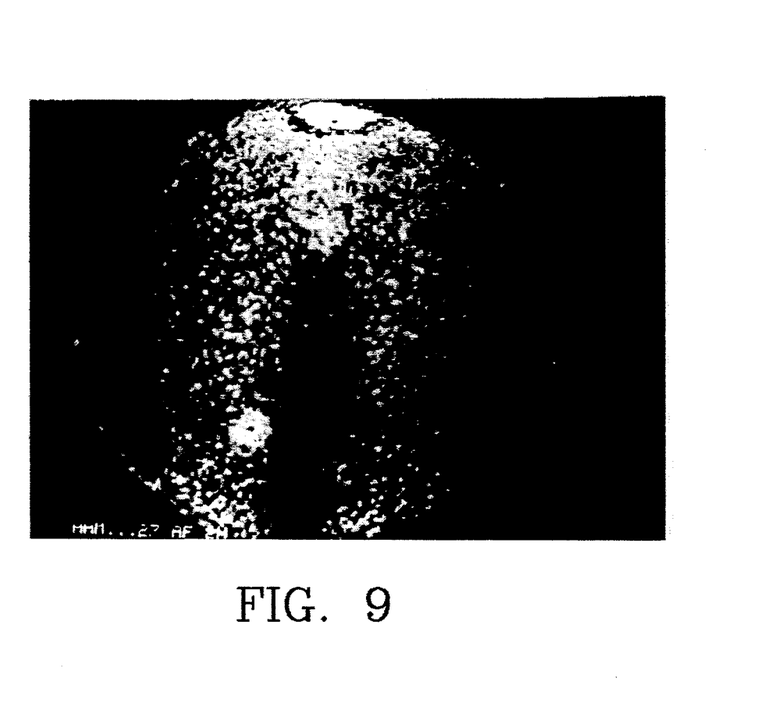
FIG. 9 shows the scintigraphy with D 25 (thighs anterior face), 4 hours after inhalation, of a metastasis in cutaneous form less than 5 mm in size in the anterointernal region of the right thigh of a patient suffering from a metastasis of an adenocarcinoma of the left lung.

FIG. 9: Patient HAM . . . : metastasis of an adenocarcinoma of the left lung. Detection by scintigraphy with D 25 (thighs ventral surface), 4 hours after inhalation, of a subcutaneous metastasis less than 5 mm in size in the anterointernal region of the right thigh.

We claim:

1. A method for detecting and locating any inflammatory and/or tumor foci in a patient which comprises administering to said patient, by nebulization for inhalation, a solution comprising a detectable component coupled to a polysaccharide compound, said polysaccharide compound selected from the group consisting of (1) the compound D 25, (2) the compound D 25 oxidized so that the galactofuranose residue therein has been converted to arabinose, (3) the amide, ester or ether derivatives of (1) or (2), (4) the quaternary ammonium derivatives and salts of (1), (2) or (3), and (5) derivatives obtained by grafting of phosphatides onto (1), (2), (3) or (4); and detecting the detectable component.

2. The method of claim 1 wherein said detectable component is selected from the group consisting of radioactive components, paramagnetic components and fluorescent components.

3. The method of claim 1 in which said administration is to a patient for the detection of sarcoidosis, alveolitis, granulomatosis, pneumocystosis, lung interstitial pathology or inflammatory and infectious lesions.

4. The method of claim 2 in which said detectable component is radioactive and said detection is by scintigraphy.

5. A method for detecting and locating any inflammatory and/or tumor foci in a patient which comprises administering to said patient, by nebulization for inhalation, a solution comprising a detectable component coupled to a polysaccharide compound, said polysaccharide compound selected from the group consisting of (1) the polysaccharide compound extracted from bacterial membrane proteoglycon of bacteria *Klebsiella pneumoniae*, such as deposited at the National Collection of the Pasteur Institute, under No. I-145, composed essentially of galactose units and having a molecular weight of 30 $\pm$10 KD, (2) the compound D 25 oxidized so that the galactofuranose residue therein has been converted to arabinose, (3) the amide, ester or ether derivatives of (1) or (2), (4) the quaternary ammonium derivatives and salts of (1), (2) or (3), and (5) derivatives obtained by grafting of phosphatides onto (1), (2), (3) or (4); and detecting the detectable component.

6. The method of claim 5 wherein said detectable component is selected from the group consisting of radioactive components, paramagnetic components and fluorescent components.

7. The method of claim 5 in which said administration is to a patient for the detection of sarcoidosis, alveolitis, granulomatosis, pneumocystosis, lung interstitial pathology or inflammatory and infectious lesions.

8. The method of claim 5 in which said detectable component is radioactive and said detection is by scintigraphy.

* * * * *

UNITED STATES PATENT AND TRADEMARK OFFICE
CERTIFICATE OF CORRECTION

PATENT NO. : 5,362,474
DATED : November 8, 1994
INVENTOR(S) : D'Hinterland et al.

It is certified that error appears in the above-indentified patent and that said Letters Patent is hereby corrected as shown below:

Column 5, line 6, please delete [wellas] and insert --well as--.

Column 5, line 57, please delete [P] and begin a new paragraph with the words beginning --As will be seen...--.

Column 8, line 46, delete [pneunocystosis] and insert --pneumocystosis--.

Signed and Sealed this

Second Day of May, 1995

Attest:

BRUCE LEHMAN

Attesting Officer

Commissioner of Patents and Trademarks